US011542217B2

(12) United States Patent
Bru Roig et al.

(10) Patent No.: US 11,542,217 B2
(45) Date of Patent: Jan. 3, 2023

(54) DODECA-4,8,11-TRIEN-1-OL AND ITS USE AS AROMA CHEMICAL

(71) Applicant: BASF SE, Ludwigshafen am Rhein (DE)

(72) Inventors: Miriam Bru Roig, Ludwigshafen am Rhein (DE); Ralf Pelzer, Lampertheim (DE); Florian Garlichs, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/312,779

(22) PCT Filed: Dec. 10, 2019

(86) PCT No.: PCT/EP2019/084411
§ 371 (c)(1),
(2) Date: Jun. 10, 2021

(87) PCT Pub. No.: WO2020/120469
PCT Pub. Date: Jun. 18, 2020

(65) Prior Publication Data
US 2022/0048842 A1  Feb. 17, 2022

(30) Foreign Application Priority Data
Dec. 11, 2018  (EP) .................................... 18211704

(51) Int. Cl.
*C07C 33/02*  (2006.01)
(52) U.S. Cl.
CPC .................................. *C07C 33/02* (2013.01)

(58) Field of Classification Search
CPC ....................................................... C07C 33/02
See application file for complete search history.

(56) References Cited

U.S. PATENT DOCUMENTS

| 8,212,082 B2 * | 7/2012 | Teles ....................... C07C 45/82 |
| | | 568/469.9 |
| 2010/0190869 A1 * | 7/2010 | Teles ....................... C07C 45/62 |
| | | 568/469.9 |

FOREIGN PATENT DOCUMENTS

| DE | 10322635 A1 | 12/2004 |
| WO | 2010/086313 A1 | 8/2010 |

OTHER PUBLICATIONS

International Preliminary Report on Patentability received for PCT Patent Application No. PCT/EP2019/084411, dated Jun. 24, 2021, 7 pages.
International Search Report and Written Opinion received for PCT Patent Application No. PCT/EP2019/084411, dated Mar. 9, 2020, 8 pages.

* cited by examiner

*Primary Examiner* — Yate' K Cutliff
(74) *Attorney, Agent, or Firm* — Faegre Drinker Biddle & Reath LLP

(57) ABSTRACT

The present invention relates to dodeca-4,8,11-trien-1-ol and a method of preparing same, to the use of dodeca-4,8,11-trien-1-ol as aroma chemical; to the use of dodeca-4,8,11-trien-1-ol for preparing an aroma chemical composition or for modifying the aroma character of an aroma chemical composition; to an aroma chemical composition containing dodeca-4,8,11-trien-1-ol; and to a method of preparing an aromatized composition or for modifying the aroma character of an aromatized composition.

16 Claims, No Drawings

DODECA-4,8,11-TRIEN-1-OL AND ITS USE AS AROMA CHEMICAL

CROSS-REFERENCE TO RELATED APPLICATIONS

This application is a national stage application (under 35 U.S.C. § 371) of PCT/EP2019/084411, filed Dec. 10, 2019, which claims benefit of European Application No. 18211704.4, filed Dec. 11, 2018, both of which are incorporated herein by reference in their entirety.

The present invention relates to dodeca-4,8,11-trien-1-ol and a method of preparing same, to the use of dodeca-4,8,11-trien-1-ol as aroma chemical; to the use of dodeca-4,8,11-trien-1-ol for preparing an aroma chemical composition or for modifying the aroma character of an aroma chemical composition; to an aroma chemical composition containing dodeca-4,8,11-trien-1-ol; and to a method of preparing an aromatized composition or for modifying the aroma character of an aromatized composition.

TECHNICAL BACKGROUND

Aroma chemicals, especially fragrances, are of great interest especially in the field of cosmetics and cleaning and laundry compositions. Fragrances of natural origin are mostly expensive, often limited in their available amount and, on account of fluctuations in environmental conditions, are also subject to variations in their content, purity etc. To circumvent these undesirable factors, it is therefore of great interest to create synthetic substances which have organoleptic properties that resemble more expensive natural fragrances or which have novel and interesting organoleptic profiles.

Despite a large number of already existing synthetic aroma chemicals (fragrances and flavorings), there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should also have additional positive secondary properties, such as e.g. an efficient preparation method, the possibility of providing better sensory profiles as a result of synergistic effects with other fragrances, a higher stability under certain application conditions, a higher extendability, a better higher substantivity, etc.

Certain fatty alcohols and fatty aldehydes have desirable olfactory properties and are used in fragrances and/or flavorings. For example, pelargonic alcohol (1-nonanol) and decanal are widely used to confer citrus-like aromas. Further, a mixture comprising stereoisomers of the triple unsaturated, straight-chain aldehyde dodeca-4,8,11-trienal has been described to have an odor reminiscent of fir needles and wood (WO 2010/086313).

However, since even small changes in chemical structure bring about massive changes in the sensory properties such as odor and also taste, the targeted search for substances with certain sensory properties such as a certain odor is extremely difficult.

The search for new fragrances and flavorings is therefore in most cases difficult and laborious without knowing whether a substance with the desired odor and/or taste will even actually be found.

It was an object of the present invention to provide new aroma chemicals. These should have pleasant organoleptic properties. It was a further object of the present invention to provide substances which can be used as an aroma chemical in ready-to-use compositions. In particular, odor-intensive substances having a pleasant odor are sought. Furthermore, they should be combinable with other aroma chemicals, allowing the creation of novel advantageous sensory profiles. In addition, these aroma chemicals should be obtainable from readily available starting materials, allowing their fast and economic manufacturing.

This object is achieved by the provision of the novel compound dodeca-4,8,11-trien-1-ol. The inventors found that this compound has a pleasant odor reminiscent of violet leaf and green beans with aldehydic and marine elements.

SUMMARY OF THE INVENTION

Thus, a first aspect of the present invention relates to a compound which is a stereoisomer of doceca-4,8,11-trien-1-ol.

A second aspect of the present invention relates to an aroma chemical composition comprising the compound of the present invention and (i) at least one additional aroma chemical different from dodeca-4,8,11-trien-1-ol, or (ii) at least one non-aroma chemical carrier (which is preferably selected from surfactants, oil components and solvents), or (iii) at least one anti-oxidant, or (iv) at least one deodorant-active agent, or (v) a mixture of at least two of the components (i) to (iv).

A third aspect of the present invention relates to the use of a compound of the present invention as an aroma chemical, in particular as a fragrance.

A fourth aspect of the present invention relates to the use of a compound of the present invention for preparing an aroma chemical composition, in particular a fragranced composition.

A fifth aspect of the present invention relates to the use of a compound of the present invention for modifying the aroma character of an aroma chemical composition, in particular for modifying the scent character of a composition.

A $6^{th}$ aspect of the present invention relates to a method of preparing the compound of the present invention. Said method comprises the step of reacting dodeca-4,8,11-trienal with a reduction agent selective for the reduction of carbonyl groups, especially aldehyde groups, such as $NaBH_4$ or $LiAlH_4$, so as to obtain dodeca-4,8,11-trien-1-ol and, optionally, the further step of isolating the dodeca-4,8,11-trien-1-ol.

A $7^{th}$ aspect of the present invention relates to a method of preparing an aroma chemical composition. Said method comprises the step of mixing the compound of the present invention with other ingredients such as, e.g., at least one other aroma chemical and/or at least one non-aroma chemical carrier so as to obtain the aroma chemical composition.

A $8^{th}$ aspect of the present invention relates to a method of modifying the aroma of an aroma chemical composition. Said method comprises the step of incorporating the compound of the present invention into an aroma chemical composition so as to obtain an aroma-modified aroma chemical composition.

A $9^{th}$ aspect of the present invention relates to a method of modifying the aroma of a ready-to-use composition. Said method comprises the step of incorporating the compound of the present invention into a ready-to-use composition so as to obtain an aroma-modified ready-to-use composition.

The compound of the present invention and aroma chemical compositions thereof possess advantageous organoleptic properties, in particular a pleasant aroma. Therefore, they can be favorably used as aromatizing ingredients in perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions, crop protection compositions and other ready-to-use compositions.

The pleasant aroma, low volatility and excellent solubility make the compound of the present invention a suitable ingredient in compositions where a pleasing aroma is desirable. By virtue of its physical properties, the compound of the invention is well combinable with other aroma chemicals and customary ingredients in aromatized ready-to-use compositions such as, in particular, perfume compositions, This allows, e.g., the creation of aroma compositions, in particular perfume compositions having novel advantageous sensory profiles.

Furthermore, the compound of the present invention can be produced in good yields and purities by a simple synthesis starting from readily available starting materials. Thus, the compound of the present invention can be produced in large scales and in a simple and cost-efficient manner.

DETAILED DESCRIPTION OF THE INVENTION

Unless specified otherwise herein, a "compound" described herein and designations of compounds which are not stereospecific, such as "doceca-4,8,11-trien-1-ol" or "doceca-4,8,11-trienal", are not limited to any particular stereoisomer or particular mixture of stereoisomers. For example, unless specified otherwise herein, the term "doceca-4,8,11-trien-1-ol" refers to one or more stereoisomers of doceca-4,8,11-trien-1-ol. Thus, the compound of the present invention can be a single stereoisomer of doceca-4,8,11-trien-1-ol selected from (4Z,8E)-dodeca-4,8,11-trien-1-ol, (4E,8Z)-dodeca-4,8,11-trien-1-ol, (4E,8E)-dodeca-4,8,11-trien-1-ol and (4Z,8Z)-dodeca-4,8,11-trien-1-ol, or can be a mixture of two or more of these stereoisomers of doceca-4,8,11-trien-1-ol.

In particular embodiments, the compound of the present invention is (4Z,8E)-dodeca-4,8,11-trien-1-ol or (4E,8Z)-dodeca-4,8,11-trien-1-ol, or a mixture of two or more stereoisomers of doceca-4,8,11-trien-1-ol comprising (4Z,8E)-dodeca-4,8,11-trien-1-ol and (4E,8Z)-dodeca-4,8,11-trien-1-ol.

In the mixtures comprising (4Z,8E)-dodeca-4,8,11-trien-1-ol and (4E,8Z)-dodeca-4,8,11-trien-1-ol, (4Z,8E)-dodeca-4,8,11-trien-1-ol and (4E,8Z)-dodeca-4,8,11-trien-1-ol are present in a molar ratio (or weight ratio, which is the same in the present case) of preferably from 10:1 to 1:10, more preferably from 5:1 to 1:5, even more preferably from 3:1 to 1:2, in particular from 2:1 to 1:1 and specifically of approximately 3:2. "Approximately" means to include uncertainties such as due to measuring errors or precision margins of the apparatuses used for determining the ratio (such as NMR; GC HPLC etc.).

In a particular embodiment, the compound of the present invention is a mixture comprising (4Z,8E)-dodeca-4,8,11-trien-1-ol and (4E,8Z)-dodeca-4,8,11-trien-1-ol. In this mixture, (4Z,8E)-dodeca-4,8,11-trien-1-ol and (4E,8Z)-dodeca-4,8,11-trien-1-ol are present in a weight (or molar) ratio of preferably from 10:1 to 1:10, more preferably from 5:1 to 1:5, even more preferably from 3:1 to 1:2, in particular from 2:1 to 1:1 and specifically of approximately 3:2.

Mixtures comprising the (4Z,8E) and the (4E,8Z) isomer may further comprise (4E,8E)-dodeca-4,8,11-trien-1-ol, or (4Z,8Z)-dodeca-4,8,11-trien-1-ol, or both (4E,8E)-dodeca-4,8,11-trien-1-ol and (4Z,8Z)-dodeca-4,8,11-trien-1-ol.

In a particular embodiment, the (4E,8E) and (4Z,8Z) isomers, if at all present, are contained in rather minor amounts; to be more precise in an amount of in sum [i.e. total amount of (4E,8E) and (4Z,8Z)] at most 20% by weight, preferably at most 10% by weight, in particular at most 5% by weight, specifically at most 2% by weight and very specifically at most 1% by weight, relative to the total weight of all four stereoisomers (4Z,8E), (4E,8Z), (4E,8E) and (4Z,8Z).

In a particular embodiment of the mixtures comprising (4Z,8E)-dodeca-4,8,11-trien-1-ol and (4E,8Z)-dodeca-4,8,11-trien-1-ol, these two stereoisomers account preferably for at least 80% by weight, more preferably for at least 90% by weight, in particular for at least 95% by weight, specifically for at least 98% by weight and very specifically for at least 99% by weight of the total weight of the mixture. The remainder to 100% is mostly composed of one or both of the other stereoisomers [(4E,8E) and (4Z,8Z)].

The compound of the present invention, as defined herein, is useful as an aroma chemical.

In the context of the present invention, the term "aroma" refers to a scent (also termed "perfume" or "fragrance") and/or a flavor. Likewise, the term "aromatized" as used herein means scented (also termed "perfumed" or "fragranced") and/or flavored. According to preferred embodiments of the present invention, the term "aroma" specifically refers to a scent, and the term "aromatized" specifically means scented.

The term "aroma chemical" as used herein denotes a substance which is used to obtain an olfactory and/or flavor impression, in particular a scent or flavor impression. The term "olfactory" denotes an odor impression without any positive or negative judgement, while the terms "scent", "fragrance" and "perfume" as used herein are connected to an odor impression which is generally felt as pleasant. A flavor induces a taste impression.

"Pleasant odor", "pleasant odor impression", "pleasant odiferous properties" are hedonistic expressions which describe the niceness and conciseness of an odor impression conveyed by an aroma chemical. The more general hedonistic expressions "advantageous sensory properties" or "advantageous organoleptic properties" describe the niceness and conciseness of an organoleptic impression conveyed by an aroma chemical. "Niceness" and "conciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typically tart apple can also be concise. If both reactions arise upon smelling the substance, in the example thus a nice and concise apple odor, then this substance has particularly advantageous sensory properties.

The term "odor-intensive substances" refers to substances or aroma chemicals exhibiting intense odor impressions. Intense odor impressions are to be understood as meaning those properties of aroma chemicals which permit a striking perception even in very low gas space concentrations. The intensity can be determined via a threshold value determination. A threshold value is the concentration of a substance in the relevant gas space at which an odor impression can just still be perceived by a representative test panel, although it no longer has to be defined. A substance class which probably belongs to the most odor-intensive known substance classes, i.e. has very low odor threshold values, are thiols, whose threshold value is often in the ppb/m$^3$ range.

Expediently, the compound of the present invention or an aroma chemical composition comprising said compound is used as a fragrance.

In particular, the compound of the present invention is used to impart a note that is reminiscent of violet leaf and green beans with aldehydic and marine elements; or is used to produce a scent that is reminiscent of violet leaf and green beans with aldehydic and marine elements.

The compound of the present invention can generally be used in a ready-to-use composition, in particular in an aromatized ready-to-use composition. "Aromatized ready-to-use composition", as used herein, refers to a ready-to-use composition which predominately induces a pleasant odor and/or taste impression. In preferred embodiments, the aromatized ready-to-use composition is a scented ready-to-use composition, i.e. induces a pleasant odor.

Scented ready-to-use compositions are for example compositions used in personal care, in home care, in industrial applications as well as compositions used in other applications, such as pharmaceutical compositions or crop protection compositions.

Preferably, the compound of the present invention is used in a composition selected from the group consisting of perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions and crop protection compositions. The compound of the present invention is used as an aroma chemical, preferably as a fragrance, in the above compositions.

In particular, the compound of the present invention is used to impart a note that is reminiscent of violet leaf and green beans with aldehydic and marine elements to the above-listed compositions.

Details to the above-listed compositions are given below.

Similarly, the compound of the invention can improve the sensory profiles of aroma chemical compositions as a result of synergistic effects with other aroma chemical (e.g., other fragrances) comprised in the compositions, which means that the compound can provide a booster effect for said other aroma chemicals. The compound is therefore suitable as a booster for other aroma chemicals.

Accordingly, the invention also relates to the use of the compound of the invention for modifying the aroma character (e.g., the scent character) of an aromatized (e.g., fragranced) composition; and specifically to the use as a booster for other aroma chemicals.

Booster effect of a substance means that the substance enhances and intensifies in aroma chemical formulations (such as, e.g., perfumery formulations) the overall sensory (e.g., olfactory) impression of the formulation. In the mint range, for example, it is known that menthyl methyl ether intensifies the perfumery or taste mixtures of peppermint oils and particularly in top notes brings about a considerably more intensive and more complex perception although the ether itself, being a pure substance, develops no particular intensive odor at all. In fragrance applications, Hedione® (methyl dihydrojasmonate), which as a pure substance only exhibits a light floral jasmin note, reinforces diffusion, freshness and volume of a perfume composition as an odor booster. Booster effects are particularly desired when top-note-characterized applications are required, in which the odor impression is to be conveyed particularly quickly and intensively, for example in deodorants, air fresheners or in the taste sector in chewing gums.

To achieve such a booster effect, the compound of the invention can be used, for example, in an amount of 0.001 to 10 wt % (weight-%), such as in an amount of 0.01 to 2 wt %, preferably from 0.05 to 1 wt %, in particular in an amount of from 0.1 to 0.5 wt %, based on the total weight of the resulting aroma chemical composition.

Furthermore, the compound of the invention can have further positive effects on the composition in which it is used. For example, the compound can enhance the overall performance of the composition into which it is incorporated, such as the stability, e.g. the formulation stability, the extendability or the staying power of the composition.

In another aspect, the present invention relates to an aroma chemical composition comprising the compound of the invention and:
  (i) at least one additional aroma chemical, or
  (ii) at least one non-aroma chemical carrier, or
  (iii) at least one anti-oxidant, or
  (iv) at least one deodorant-active agent, or
  (v) a mixture of at least two of components (i) to (iv)).

The term "aroma chemical composition", as used herein, refers to a composition which induces a pleasant aroma, e.g., a pleasant odor impression.

The non-aroma chemical carrier in the aroma chemical composition of the invention can be, in particular, selected from surfactants, oil components and solvents.

The additional aroma chemical is of course different from dodeca-4,8,11-trien-1-ol, i.e. is neither a stereoisomer of dodeca-4,8,11-trien-1-ol nor a mixture of two or more stereoisomers of dodeca-4,8,11-trien-1-ol.

By virtue of its physical properties, the compound of the invention, dodeca-4,8,11-trien-1-ol, is well combinable with other aroma chemicals (e.g., other fragrances) and other customary ingredients in aromatized (e.g., fragranced) ready to use compositions such as, in particular, perfume compositions. This allows, e.g., the creation of aroma compositions (e.g., perfume compositions) which have novel advantageous sensory profiles. Especially, as already explained above, the compound can provide a booster effect for other aroma chemicals (such as other fragrances).

Accordingly, in one preferred embodiment, the aroma chemical composition comprises a compound of the present invention, as defined herein; and at least one additional aroma chemical that is different from dodeca-4,8,11-trien-1-ol.

The additional aroma chemical can for example be one, preferably 2, 3, 4, 5, 6, 7, 8 or further aroma chemicals, selected from the group consisting of:

Geranyl acetate (3,7-Dimethyl-2,6 octadien-1yl acetate), alpha-hexylcinnamaldehyde, 2-phenoxyethyl isobutyrate (Phenirat$^1$), dihydromyrcenol (2,6-dimethyl-7-octen-2-ol), methyl dihydrojasmonate (preferably with a content of cis isomer of more than 60 wt %) (Hedione[9], Hedione HC[9]), 4,6,6,7,8,8-hexamethyl-1,3,4,6,7,8-hexahydro-cyclopenta[g]benzopyran (Galaxolid[3]), tetrahydrolinalool (3,7-dimethyloctan-3-ol), ethyl-linalool, benzyl salicylate, 2-methyl-3-(4-tert-butylphenyl)propanal (Lysmeral[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melonal[2]), borneol, 3-(3-isopropylphenyl)butanal (Florhydral[2]), 2-methyl-3-(3,4-methylenedioxyphenyl)-propanal (Helional[3]), 3-(4-ethylphenyl)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70 wt %) or more and 2,5,5-trimethyl-1,2,3,4,4a,5,6,7-octahydronaphthalen-2-ol (Ambrinol S[1]). Within the context of the present invention, the aforementioned aroma chemical(s) are accordingly preferably combined with the compound of the present invention as defined herein.

A further embodiment of the invention relates to a composition comprising the compound of the present invention as described herein and at least one additional aroma chemical selected from the group consisting of methyl benzoate, benzyl acetate, geranyl acetate, 2-isobutyl-4-methyltetrahydro-2H-pyran-4-ol and linalool.

A further embodiment of the invention relates to a composition comprising the compound of the present invention as described herein and 2-isobutyl-4-methyltetrahydro-2H-pyran-4-ol.

A further embodiment of the invention relates to a composition comprising the compound of the present invention as described herein and methyl benzoate.

Where trade names are given above, these refer to the following sources:
[1] trade name of Symrise GmbH, Germany;
[2] trade name of BASF SE;
[3] trade name of International Flavors & Fragrances Inc., USA;
[9] trade name of Firmenich S.A., Switzerland;
[10] trade name of PFW Aroma Chemicals B.V., the Netherlands.

Further aroma chemicals with which the compound of the present invention as described herein can be combined e.g. to give a composition according to the invention can be found e.g. in S. Arctander, Perfume and Flavor Chemicals, Vol. I and II, Montclair, N.J., 1969, self-published or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1- methoxypropoxy)-hex3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl iso-valerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl-acetals of geranial, neral, 7-hydroxy-3,7-dimethyloctanal;

the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methano-naphthalene-8(5H)-one; 2-methyl-4-(2,6,6-trimethyl-1-cyclohexen-1-yl)-2-butenal; noot-katone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclodo-decyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo-[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cyclo-heptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclo-hexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and transmethyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the aralipatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol;

1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxy-benzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)-ethanone; 2-benzofuranylethanone; (3-methyl-2-benzofuranyl)ethanone; benzo-phenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl) propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropyl-pyrazine; 2-isobutyl-3-methoxy-pyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl iso-butyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Advantageous are combinations with aroma chemicals with a fresh note, sea note, ozonic note, outdoors note and/or green floral note, such as cis-3-hexenol, 2,4-dimethylcyclohex-3-ene-1-carbaldehyde (e.g., Ligustral®, Givaudan), 1,4-bis(ethoxy-methyl)-cyclohexane (e.g., Vertofruct®, BASF) and 8-methyl-1,5-benzodioxepin-3-one (e.g., Calone®, Firmenich), the fresh, sea, ozonic, outdoors and/or green floral note of which is boosted by the compound of the present invention.

The at least one non-aroma chemical carrier can be a compound, a mixture of compounds or other additives, which have no or no noteworthy sensory properties. Typically, the at least one non-aroma chemical carrier, if present in the aroma chemical compositions according to the present invention, is a compound, a mixture of compounds or other additives, which have no or no noteworthy sensory properties. The non-aroma chemical carrier serves for the dilution and/or the fixing of the aroma chemical(s), i.e. the compounds of formula (I) and optionally one or more further aroma chemical different from compounds (I), as defined above, comprised in the aroma chemical composition.

Suitable carrier materials can be liquid or oil-like carrier materials as well as wax-like or solid carrier materials.

In particular, the non-aroma chemical carrier, if present in the compositions according to the present invention, is selected from the group consisting of surfactants, oil components and solvents.

Accordingly, a further aspect of the invention is directed to a composition comprising the compound of the present invention as described herein and at least one component selected from the group consisting of surfactants, emollients (oil component) and solvents.

One embodiment of the invention is directed to a composition comprising the compound of the present invention as described herein and at least one solvent.

In the context of the present invention, a "solvent" serves for the dilution of the compound of the present invention to be used according to the invention without having its own odiferous properties. Some solvents have fixing properties at the same time.

The one or more solvent(s) can be present in the composition from 0.01 to 99 wt % based on the composition. In a preferred embodiment of the invention, the composition comprises 0.1 to 90 wt %, preferably 0.5 to 80 wt % of solvent(s) based on the total weight of the composition. The amount of solvent(s) can be chosen depending on the composition. In one embodiment of the invention, the composition comprises 0.05 to 10 wt %, preferably 0.1 to 5 wt %, more preferably 0.2 to 3 wt % based on the total weight of the composition. In one embodiment of the invention, the composition comprises 20 to 70 wt %, preferably 25 to 50 wt % of solvent(s) based on the total weight of the composition.

Preferred solvents are ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB).

Especially preferred solvents are selected from the group consisting of ethanol, propylene glycol, dipropylene glycol, triethyl citrate, benzyl benzoate and isopropyl myristate.

In a preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

According to a further aspect, the compound of the present invention is suitable for use in surfactant-containing compositions. According to its characteristic scent profiles, the compound can especially be used for the perfuming of surfactant-containing compositions such as, for example, cleaners (in particular laundry care products and all-purpose cleaners).

One embodiment of the invention is therefore directed to a composition comprising the compound of the present invention as described herein and at least one surfactant.

The surfactant(s) may be selected from anionic, nonionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in a quantity of 0 to 40 wt %, preferably 0 to 20 wt %, more preferably 0.1 to 15 wt %, and particularly 0.1 to 10 wt %, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, co-coacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_8$ to $C_{18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalk-ylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12}$-$C_{18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trim ethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising the compound of the present invention as described herein and at least one oil component.

The oil components are typically present in a total quantity of 0.1 to 80 wt %, preferably 0.5 to 70 wt %, more preferably 1 to 60 wt %, even more preferably 1 to 50 wt %, in particular 1 to 40 wt %, more particularly 5 to 25 wt % and specifically 5 to 15 wt % based on the total weight of the composition.

The oil components may be selected, for example, from Guerbet alcohols based on fatty alcohols containing 6 to 18, preferably 8 to 10, carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, stearyl myristate, stearyl palmitate, stearyl stearate, stearyl isostearate, stearyl oleate, stearyl behenate, stearyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$ alkyl-hydroxycarboxylic acids with linear or branched $C_6$-$C_{22}$ fatty alcohols, more especially dioctyl malate, esters of linear and/or branched fatty acids with polyhydric alcohols (for example propylene glycol, dimer dial or trimer triol), triglycerides based on $C_6$-$C_{10}$ fatty acids, liquid mono-, di- and triglyceride mixtures based on $C_6$-$C_{18}$ fatty acids, esters of $C_6$-$C_{22}$ fatty alcohols and/or Guerbet alcohols with aromatic carboxylic acids, more particularly benzoic acid, esters of dicarboxylic acids with polyols containing 2 to 10 carbon atoms and 2 to 6 hydroxyl groups, vegetable oils, branched primary alcohols, substituted cyclohexanes, linear and branched $C_6$-$C_{22}$ fatty alcohol carbonates such as, for example, dicaprylyl carbonate (Cetiol® CC), Guerbet carbonates based on fatty alcohols containing 6 to 18, preferably 8 to 10, carbon atoms, esters of benzoic acid with linear and/or branched $C_6$ to $C_{22}$ alcohols (for example Finsolv® TN), linear or branched, symmetrical or nonsymmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

The compound of the invention can also be used together with an anti-oxidant.

Anti-oxidants are able to inhibit or prevent the undesired changes in the compositions to be protected caused by oxygen effects and other oxidative processes. The effect of the anti-oxidants consists in most cases in them acting as free-radical scavengers for the free radicals which arise during autoxidation.

Anti-oxidants can for example be selected from the group consisting of
  amino acids (for example glycine, alanine, arginine, serine, threonine, histidine, tyrosine, tryptophan) and derivatives thereof,
  imidazoles (e.g. urocanic acid) and derivatives thereof,
  peptides, such as D,L-carnosine, D-carnosine, L-carnosine (=β-Alanyl-L-histidin) and derivatives thereof,
  carotenoids, carotenes (e.g. alpha-carotene, beta-carotene, lycopene, lutein) or derivatives thereof,
  chlorogenic acid and derivatives thereof,
  lipoic acid and derivatives thereof (for example dihydrolipoic acid),
  auro-thioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and salts thereof,
  dilauryl thiodipropionate, distearyl thiodipropionate, thiodipropionic acid and derivatives thereof (esters, ethers, peptides, lipids, nucleotides, nucleosides and salts),
  sulfoximine compounds (for example buthionine sulfoximines, homocysteine sulfoximine, buthionine sulfones, penta-, hexa-, heptathionine sulfoximine),
  (metal) chelating agents (e.g. alpha-hydroxy fatty acids, palmitic acid, phytic acid, lactoferrin),
  alpha-hydroxy acids (for example citric acid, lactic acid, malic acid),
  humic acid, bile acid, bile extracts, bilirubin, biliverdin, boldin (=alkaloid from the plant *Peumus boldus*, boldo extract,
  EDTA, EGTA and derivatives thereof,
  unsaturated fatty acids and derivatives thereof (e.g. gamma-linolenic acid, linoleic acid, oleic acid),
  folic acid and derivatives thereof,
  ubiquinone and ubiquinol and derivatives thereof,
  vitamin C and derivatives (for example ascorbyl palmitate, Mg ascorbyl phosphate, ascorbyl acetate),
  tocopherols and derivatives (for example vitamin E acetate),
  vitamin A and derivatives (for example vitamin A palmitate),
  coniferyl benzoate of gum benzoin, rutic acid and derivatives thereof, alpha-glycosylrutin, ferulic acid, furfurylideneglucitol,
  butylhydroxytoluene (BHT), butylhydroxyanisole (BHA),
  nordihydroguaiacic acid, nordihydroguaiaretic acid, trihydroxybutyrophenone, uric acid and derivatives thereof, mannose and derivatives thereof,
  superoxide dismutase,
  zinc and derivatives thereof (for example ZnO, $ZnSO_4$),
  selenium and derivatives thereof (for example selenomethionine) and
  stilbenes and derivatives thereof (e.g. stilbene oxide, trans-stilbene oxide).

In a preferred embodiment, the anti-oxidant is selected from the group consisting of pentaerythrityl, tetra-di-t-butyl hydroxyhydrocinnamate, nordihydroguaiaretic acid, ferulic acid, resveratrol, propyl gallate, butylhydroxytoluene (BHT), butylhydroxyanisole (BHA), ascorbyl palmitate and tocopherol.

The compositions according to the invention can comprise the anti-oxidants in an amount of 0.001 to 25 wt.-%, preferably 0.005 to 10 wt.-%, preferably 0.01 to 8 wt.-%, preferably 0.025 to 7 wt.-%, preferably 0.05 to 5 wt.-%, based on the total weight of the composition.

The compound of the invention can also be used together with deodorizing compositions.

Deodorizing compositions (deodorants and antiperspirants) counteract, mask or eliminate body odors. Body odors are formed through the action of skin bacteria on apocrine perspiration which results in the formation of unpleasant-smelling degradation products.

Another embodiment of the invention is therefore directed to a composition comprising the compound of the invention and at least one deodorant-active agent.

In a preferred embodiment of the invention, the at least one deodorant-active agent is selected from the groups consisting of anti-perspirants, esterase inhibitors and anti-bacterial agents.

Suitable antiperspirants can be selected from the group consisting of salts of aluminium, zirconium or zinc. Examples are aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Aluminium chlorohydrate, aluminium zirconium tetrachlorohydrate, aluminium zirconium pentachlorohydrate and complex compounds thereof are preferably used.

In a preferred embodiment of the invention the compositions comprise at least one antiperspirant selected from the group consisting aluminium chloride, aluminium chlorohydrate, aluminium dichlorohydrate, aluminium sesquichlorohydrate, aluminium hydroxyallantoinate, aluminium chloride tartrate, aluminium zirconium trichlorohydrate, aluminium zirconium tetrachlorohydrate and aluminium zirconium pentachlorohydrate.

The compositions according to the invention can comprise the antiperspirants in an amount of 1 to 50, preferably 5 to 30 and more particularly 10 to 25 wt.-%, based on the solids content of the composition.

Where perspiration is present in the underarm region, extracellular enzymes-esterases, mainly proteases and/or lipases are formed by bacteria and split the esters present in the perspiration, releasing odors in the process. Suitable esterase inhibitors are for example trialkyl citrates, such as trimethyl citrate, tripropyl citrate, triisopropyl citrate, tributyl citrate and, in particular, triethyl citrate. Esterase inhibitors inhibit enzyme activity and thus reduce odor formation. The free acid is probably released by the cleavage of the citric acid ester and reduces the pH value of the skin to such an extent that the enzymes are inactivated by acylation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

In a preferred embodiment of the invention the compositions comprise at least one esterase inhibitor selected from the group consisting of trimethyl citrate, tripropyl citrate, triisopropyl citrate, tributyl citrate triethyl citrate, lanosterol, cholesterol, campesterol, stigmasterol, sitosterol sulfate, sitosterol phosphate, glutaric acid, glutaric acid monoethyl ester, glutaric acid diethyl ester, adipic acid, adipic acid monoethyl ester, adipic acid diethyl ester, malonic acid, malonic acid diethyl ester, citric acid, malic acid, tartaris acid, tartaric acid diethyl ester and zinc glycinate.

The compositions according to the invention can comprise the esterase inhibitors in amounts of 0.01 to 20, preferably 0.1 to 10 and more particularly 0.5 to 5 wt.-%, based on the solids content of the composition.

The term "anti-bacterial agents" as used herein encompasses substances which have bactericidal and/or bacteriostatic properties. Typically these substances act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

In a preferred embodiment the antibacterial agent is selected from the group consisting of chitosan, phenoxyethanol, 5-Chloro-2-(2,4-dichlorophenoxy)-phenol, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1, 2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides.

The compositions according to the invention can comprise the antibacterial agents in amounts of 0.01 to 5 wt. % and preferably 0.1 to 2 wt.-%, based on the solids content of the composition.

Dodeca-4,8,11-trien-1-ol can be prepared by standard methods of organic chemistry and by methods as described in the art. To be more precise, dodeca-4,8,11-trien-1-ol can be prepared by subjecting the corresponding dodeca-4,8,11-trienal to a reduction that selectively converts the carbonyl group to a hydroxyl group. Suitable methods for selective reduction of a carbonyl group in compounds comprising C=C double bonds to obtain the corresponding (unsaturated) alcohols are well known to a person skilled in the art. For example, the reduction of the carbonyl group may be achieved by reacting the dodeca-4,8,11-trienal with a boron hydride such as lithium, sodium or potassium tetrahydroborate or with an aluminum hydride such as lithium aluminum hydride, DIBAL-H or $LiAlH[OC(CH_3)_3]_3$. The reaction can be performed, e.g., in analogy to the method described by S. Krishnamurthy et al. Org. Chem., 1977, 42 (7), pp 1197-1201, J. C. Fuller et al. Tetrahedron Lett. 34, 1993, 257-260, B. Zeynidazeh et al. Bull. Korean Chem. Soc. 24 (3), 2003, 295-298. Preferably, $NaBH_4$ or $LiAlH_4$ is used. According to a particular embodiment, the reduction of the C=O (carbonyl) group of dodeca-4,8,11-trienal is carried out using $NaBH_4$.

The reduction of the C=O (carbonyl) group of dodeca-4,8,11-trienal is preferably carried out in an organic solvent. Suitable organic solvents are all those which do not interfere in the reaction, especially those which are not prone to reduction themselves so as to compete with the trienal. Moreover, they have to be compatible with the reduction agent used. For example, if $LiAlH_4$ is used, seeing its easy hydrolyzability, the solvent has to be anhydrous, whereas in case of the use of $NaBH_4$, which is much less reactive, the reaction can even be carried out in water or aqueous mixtures. Suitable solvents are for example alcohols, in particular alkanols or glycols, ethers, such as dimethyl ether, diethyl ether, dipropyl ether, diisopropyl ether, methyl-tert-butyl ether, tetrahydrofuran and the dioxanes, alkanes, such as pentane, hexane or heptane, cycloalkanes, such as cyclohexane or cyclooctane, and aromatic hydrocarbons, such as toluene or the xylenes, and in case of the use of $NaBH_4$ also water or mixtures of water with those of the above-listed solvents which are water-miscible. In case of the use of $NaBH_4$, preference is given to alcohols or a mixture of alcohols. Examples of said alcohols include alkanols, e.g., $C_1$-$C_4$-alkanols, such as methanol, ethanol, n-propanol, isopropanol, n-butanol, 2-butanol, isobutanol or tert.-butanol, glycols, especially mono- or di-$C_2$-$C_4$-alkylene glycols, such as ethylene glycol, propylene glycol, diethylene glycol and the like and the monoalkylethers of glycols, such as the monomethyl or monoethyl ether of ethylene glycol, propylene glycol or diethylene glycol. More preference is given to alkanols, in particular $C_1$-$C_4$-alkanols. Specifically, methanol, ethanol, isopropanol or mixtures thereof are used. Very specifically, ethanol is used. In case of the use of LiAlH$_4$, LiAlH[OC(CH$_3$)$_3$] and DIBAL-H, preference is given to the use of the above ethers, alkanes, cycloalkanes and aromatic hydrocarbons, and in particular to the above ethers and alkanes. As said, in case of LiAlH$_4$, the solvent is expediently anhydrous. Methods for removing residual water in solvents are well known in the art.

The reduction (hydrogenation) of the dodeca-4,8,11-trienal can be performed at a temperature in the range of from −20° C. to the boiling point of the reaction mixture, preferably at from 0 to 40° C., more preferably from 10 to 30° C. and in particular from 20 to 30° C. Specifically, the reduction is carried out at room temperature (20-25° C.).

The reaction pressure is not critical. Usually, the reaction is carried out at ambient pressure.

The amount of the reducing agent and the reaction time are expediently chosen so as to obtain a high yield of dodeca-4,8,11-trien-1-ol. Seeing that the preferably used LiAlH$_4$, and NaBH$_4$ can transfer all four hydride anions, dodeca-4,8,11-trienal is expediently reacted with sub-equimolar to almost equimolar amounts of NaBH$_4$ or LiAlH$_4$, e.g. amounts in the range of from 0.2 to 0.9, preferably from 0.4 to 0.9, in particular from 0.5 to 0.8, and specifically from 0.5 to 0.7 mol of NaBH$_4$ or LiAlH$_4$ per mol of dodeca-4,8, 11-trienal. It is however also possible to use the reducing agent in equimolar or higher amounts. In case of reducing agents which transfer only one hydride ion, such as LiAlH [OC(CH$_3$)$_3$] and DIBAL-H, preference is given to their use in equimolar or higher amounts, e.g. to their use in an amount of from 1 to 1.5 mol, preferably from 1 to 1.2 mol and in particular from 1 to 1.1 mol per mol of dodeca-4,8, 11-trienal.

After the reaction has sufficiently progressed, i.e. the amount of dodeca-4,8,11-trien-1-ol ideally has reached its maximum, the reaction is quenched to deactivate non-reacted reduction agent, generally by the addition of water. Work-up can be carried by customary means. For example, the organic solvent can be removed by, e.g., evaporation, if desired under reduced pressure. The hydrogenation product containing dodeca-4,8,11-trien-1-ol can be recovered by extracting the aqueous phase with a suitable organic solvent such as, e.g., ethyl acetate, which then can be removed by evaporation.

Typically, the crude product obtained from the hydrogenation is subsequently purified to remove unwanted by-products and/or impurities, such as residual starting material. Generally, purification is performed using common purification methods such as, e.g., distillation or chromatographic methods, for example column chromatography or high performance liquid chromatography.

The dodeca-4,8,11-trienal used as starting material for preparing the compound of the present invention can be prepared by methods known in the art. For example, dodeca-4,8,11-trienal can be obtained by oxidizing cyclododeca-1, 5,9-triene by means of N$_2$O and then isolating dodeca-4,8, 11-trienal from the reaction mixture. Methods for the preparation, isolation and purification of dodeca-4,8,11-trienal are described, e.g., in WO 2010/086313. Generally, cyclododeca-1,5,9-triene as a starting material is also readily available from commercial sources.

The compound of the present invention as described herein can be used in a wide range of aroma chemical compositions. The olfactory properties and the substance properties (such as solubility in customary solvents and compatibility with further customary constituents of such compositions) of dodeca-4,8,11-trien-1-ol underline its particular suitability for the stated use purposes and compositions.

Suitable aroma chemical compositions are for example perfume compositions, body care compositions, products for oral and dental hygiene, hygiene articles, cleaning compositions, textile detergent compositions, compositions for scent dispensers, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Partum.

Body care compositions include cosmetic compositions, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products such as e.g. hair-sprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams, products of decorative cosmetics such as e.g. eye-liners, eye-shadows, nail varnishes, make-ups, lipsticks and mascara.

Products for oral and dental hygiene include toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing detergents both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, softgels, gelcaps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the managing of plant diseases, weeds and other pests (both vertebrate and invertebrate) that damage agricultural crops and forestry.

The compositions according to the invention can further comprise one or more substances, such as, for example: preservatives, abrasives, anti-acne agents, agents to combat skin aging, antibacterial agents, anti-cellulite agents, anti-dandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyes, color-protection agents, pigments, anti-corrosives, polyols, surfactants, electrolytes, organic solvents or silicone derivatives.

The compound of the present invention and the aroma chemical compositions comprising same according to the present invention can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the mixture or composition of the present invention described herein, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting the mixture or composition of the present invention described herein with a suitable wax-like substance and by extrusion with subsequent solidification, optionally in a suitable solvent, e.g. isopropanol.

Generally, the total amount of the compound of the present invention described herein in the aroma chemical compositions according to the present invention is typically adapted to the particular intended use or the intended application and can, thus, vary over a wide range. As a rule, the customary standard commercial amounts for scents are used.

The compositions according to the invention can comprise the compound of the present invention described herein in an overall amount of from 0.0001 to 99.9 wt %, based on the total weight of the composition.

Aroma chemical compositions of the invention which are not directly used as, but are intended for aromatizing, ready-to-use compositions typically comprise the compound of the invention in an overall amount of from 0.01 to 5 wt %, preferably an overall amount of from 0.05 to 1 wt %, in particular an overall amount of from 0.1 to 0.5 wt %, based on the total weight of the composition.

Compositions of the invention which are ready-to-use compositions typically comprise the compound of the present invention described herein in an overall amount of from 0.0001 to 0.5 wt %, preferably an amount of from 0.0005 to 0.1 wt %, in particular from 0.001 to 0.05 wt %, based on the total weight of the composition.

A further embodiment of the invention is directed to a method of preparing an aroma chemical composition, in particular an aromatized (e.g., fragranced) composition, especially an aromatized (e.g., fragranced) ready-to-use composition, comprising incorporating the compound of the present invention described herein into an aroma chemical composition, in particular into an aromatized (e.g., fragranced) composition, especially into an aromatized (e.g., fragranced) ready-to-use composition.

For example, the method can be carried out by mixing the compound of the present invention described herein and:
(i) at least one additional aroma chemical different from dodeca-4,8,11-trien-1-ol, or
(ii) at least one non-aroma chemical carrier, or
(iii) at least one anti-oxidant, or
(iv) at least one deodorant-active agent, or
(v) a mixture of at least two of components (i) to (iv)).

The invention is also directed to a method for modifying the aroma character (e.g., scent character) of an aroma chemical composition such as, e.g., a fragranced composition, in particular a fragranced ready-to-use composition, wherein the method comprises incorporating the compound of the present invention described herein into an aroma chemical composition such as, e.g., into a fragranced composition, in particular into a fragranced ready-to-use composition.

In particular, the invention is directed to a method of preparing a perfume composition, body care composition, product for oral and dental hygiene, hygiene article, cleaning composition, textile detergent composition, composition for scent dispensers, food, food supplement, pharmaceutical composition or crop protection composition, comprising including the compound of the present invention described herein in a perfume composition, body care composition, product for oral and dental hygiene, hygiene article, cleaning composition, textile detergent composition, composition for scent dispensers, food, food supplement, pharmaceutical composition or crop protection composition.

In one embodiment the invention is directed to a method for imparting a note reminiscent of violet leaf and green beans with aldehydic and marine elements to a perfume composition, body care composition, product for oral and dental hygiene, hygiene article, cleaning composition, textile detergent composition, composition for scent dispensers, food, food supplement, pharmaceutical composition or crop protection composition, which comprises including a compound of the present invention in a perfume composition, body care composition, product for oral and dental hygiene, hygiene article, cleaning composition, textile detergent composition, composition for scent dispensers, food, food supplement, pharmaceutical composition or crop protection composition.

The following examples serve as further illustration of the invention.

EXAMPLES

1. Preparation Example

Dodeca-4,8,11-trienal was prepared and purified as described in WO 2010/086313. 100 g of dodeca-4,8,11-trienal were dissolved in 400 ml of ethanol. Then, 12.2 g of $NaBH_4$ were added in step-wise manner to the solution at room temperature. After stirring the mixture for 2.5 h at room temperature, the reaction was stopped by the addition of 300 ml of water. The ethanol was removed by evaporation and the reaction product was extracted from the aqueous phase using 300 ml of ethyl acetate. The thus obtained organic phase was washed with brine solution and then dried with sodium sulfate. After evaporation of the organic solvent, 94.6 g of crude product containing about 76% dodeca-4,8,11-trien-1-ol was obtained. The product was purified by distillation obtaining dodeca-4,8,11-trien-1-ol with a purity of 88%. The purified product was analyzed by NMR, the results indicating the presence of (4Z,8E)-dodeca-4,8,11-trien-1-ol and (4E,8Z)-dodeca-4,8,11-trien-1-ol at a ratio of 3:2.

(4Z,8E)-Dodeca-4,8,11-trien-1-ol $^{13}C$ NMR (125 MHz, $CDCl_3$): d=23.61 (C10), 27.17 (C6), 32.49 (C7), 32.51 (C11), 36.72 (C3), 62.22 (C12), 114.85 (C1), 128.04 (C4), 129.30 (C5), 129.76 (C9), 130.95(C8), 137.26 (C2).

(4E,8Z)-Dodeca-4,8,11-trien-1-ol $^{13}C$ NMR (125 MHz, $CDCl_3$): d=28.86 (C10), 27.18 (C6), 31.55 (C7), 32.32 (C11), 36.72 (C3), 62.14 (C12), 114.57 (C1), 126.92 (C4), 129.97 (C5), 130.21 (C9), 130.32(C8), 137.94 (C2).

2. Olfactory Assessment

In order to test the quality and intensity of the odor of dodeca-4,8,11-trien-1-ol, scent strip tests were performed.

For this purpose, strips of absorbent paper were dipped into a solution containing 1 to 10 wt % of the compound to be tested in ethanol. After evaporation of the solvent (about 30 s) the scent impression was olfactively evaluated by a trained perfumer.

Results

TABLE 1

Results of the scent tests

| Example no. | Compound/Isomer mixture | Odor Description |
|---|---|---|
| 1 | (4Z,8E)-dodeca-4,8,11-trien-1-ol:(4E,8Z)-dodeca-4,8,11-trien-1-ol = 3:2 | violet leaf, green beans, aldehydic, marine |

Advantageous Perfume Components

The compound of example 1 was formulated in the perfume compositions according to tables 2 and 3.

TABLE 2

Perfume oil compositions 1A and 1B

|  | 1A | 1B |
|---|---|---|
| Benzoe Siam 20% | 711 | 711 |
| Rosewood Oil brasilian | 85 | 85 |
| Copaivabalm rect. | 9 | 9 |
| Linalyl-benzoate | 31 | 31 |
| 3-cis-Hexenyl-salicylate | 21 | 21 |
| Geranyl-acetate | 47 | 47 |
| Ethyl-benzoate | 12 | 12 |
| Cinnamyl-acetate | 2 | 2 |
| Benzyl-acetate | 71 | 71 |
| Methyl-anthranilate 10% | 5 | 5 |
| Bayoil St. Thomas 10% | 5 | 5 |
| Compound of example 1 | 0 | 20 |
|  | 1000 | 1020 |

TABLE 3

Perfume oil compositions 2A and 2B

|  | 2A | 2B |
|---|---|---|
| Ethyl Caproate | 1 | 1 |
| Ethyl Acetate | 1 | 1 |
| Iso Amyl Butyrate | 1 | 1 |
| Maltol or Veltol | 1 | 1 |
| Geranyl Butyrate | 2 | 2 |
| Ethyl Vanilline 10% DPG | 2 | 2 |
| Cis 3 Hexenyl Acetate | 3 | 3 |
| Allyl Caproate | 3 | 3 |
| Verdural B 10% DPG | 3 | 3 |
| Oxyphenylon | 3 | 3 |
| Hexyl Butyrate | 4 | 4 |
| Ethyl Decadienoate 10% DPG | 4 | 4 |
| DM.B.C. Butyrate | 4 | 4 |
| Ethyl Maltol or Veltol Plus | 4 | 4 |
| Cyclaprop | 5 | 5 |
| Iso Amyl Acetate | 5 | 5 |
| Cis 3 Hexenol 10% DPG | 6 | 6 |
| D.M.B.C. Acetate | 7 | 7 |
| Aldehyde C 16 100% | 8 | 8 |
| Geranyl Propionate | 8 | 8 |
| Ethyl 2 Methyl Butyrate | 8 | 8 |
| Decalactone Gamma | 10 | 10 |
| Orange Bresil Oil | 10 | 10 |
| Ethyl Aceto Acetate | 10 | 10 |
| Linalool | 15 | 15 |
| Benzyl Acetate | 15 | 15 |
| Aldehyde C 14 100% | 20 | 20 |
| Citronellol | 25 | 25 |
| Linalyl Acetate | 30 | 30 |
| Geranyl Acetate | 35 | 35 |

TABLE 3-continued

Perfume oil compositions 2A and 2B

|  | 2A | 2B |
|---|---|---|
| Vertenex | 45 | 45 |
| Citronellyl Acetate | 50 | 50 |
| Verdox | 54 | 54 |
| Galaxolide 50 DEP | 100 | 100 |
| Hexyl Acetate | 190 | 190 |
| Mono Propylene Glycol | 300 | 300 |
| Compound of example 1 | 0 | 200 |
|  | 1000 | 1200 |

The invention claimed is:

1. A compound which is dodeca-4,8,11-trien-1-ol.

2. The compound of claim 1 which is selected from the group consisting of (4Z,8E)-dodeca-4,8,11-trien-1-ol, (4E,8Z)-dodeca-4,8,11-trien-1-ol, (4E,8E)-dodeca-4,8,11-trien-1-ol, (4Z,8Z)-dodeca-4,8,11-trien-1-ol, and mixtures of two or more thereof.

3. The compound of claim 2 which is (4Z,8E)-dodeca-4,8,11-trien-1-ol.

4. The compound of claim 2 which is (4E,8Z)-dodeca-4,8,11-trien-1-ol.

5. The compound of claim 2 which is a mixture of stereoisomers comprising (4Z,8E)-dodeca-4,8,11-trien-1-ol and (4E,8Z)-dodeca-4,8,11-trien-1-ol.

6. The compound of claim 5, where (4Z,8E)-dodeca-4,8,11-trien-1-ol and (4E,8Z)-dodeca-4,8,11-trien-1-ol are present in a molar ratio of from 10:1 to 1:10.

7. The compound of claim 5, wherein the mixture further comprises (4E,8E)-dodeca-4,8,11-trien-1-ol, or (4Z,8Z)-dodeca-4,8,11-trien-1-ol, or both (4E,8E)-dodeca-4,8,11-trien-1-ol and (4Z,8Z)-dodeca-4,8,11-trien-1-ol.

8. Aroma chemical composition comprising the compound of claim 1:
  (i) at least one additional aroma chemical different from dodeca-4,8,11-trien-1-ol, or
  (ii) at least one non-aroma chemical carrier; or
  (iii) at least one anti-oxidant, or
  (iv) at least one deodorant-active agent, or
  (v) a mixture of at least two of components (i) to (iv).

9. The aroma chemical composition of claim 8 which is an aromatized ready-to-use composition.

10. The aroma chemical composition of claim 9, wherein the aromatized ready-to-use composition is selected from perfume compositions, body care compositions, products for oral or dental hygiene, hygiene articles, cleaning compositions, textile detergent compositions, compositions for scent dispensers, foods, food supplements, pharmaceutical compositions and crop protection compositions.

11. The compound of claim 1 wherein the compound is an aroma chemical.

12. A method comprising providing the compound of claim 1 and preparing an aroma chemical composition.

13. A method comprising providing the compound of claim 1 and modifying the aroma character of an aroma chemical composition.

14. The method according to claim 12, wherein the aroma chemical composition is an aromatized ready-to-use composition.

15. The method of claim 14, wherein the aromatized ready-to-use composition is selected from perfume compositions, body care compositions, products for oral or dental hygiene, hygiene articles, cleaning compositions, textile detergent compositions, compositions for scent dispensers, foods, food supplements, pharmaceutical compositions and crop protection compositions.

16. A method of preparing the compound of claim 1 comprising the step of:
  (i) subjecting dodeca-4,8,11-trienal to a reduction reaction of the carbonyl group to a hydroxyl group so as to obtain dodeca-4,8,11-trien-1-ol,
  and, optionally, the further step of:
  (ii) isolating the dodeca-4,8,11-trien-1-ol.

* * * * *